United States Patent [19]

Krishnamurti

[11] Patent Number: 5,710,355
[45] Date of Patent: Jan. 20, 1998

[54] METHOD OF MAKING CHLOROBENZENES

[75] Inventor: Ramesh Krishnamurti, Williamsville, N.Y.

[73] Assignee: Occidental Chemical Corporation, Niagara Falls, N.Y.

[21] Appl. No.: 660,994

[22] Filed: Jun. 10, 1996

[51] Int. Cl.$^6$ .................... C07C 22/08; C07C 25/08; C07C 25/10
[52] U.S. Cl. .................... 570/208; 570/209; 570/201; 570/191; 570/194
[58] Field of Search .................... 570/182, 191, 570/194, 209, 208, 201

[56] References Cited

U.S. PATENT DOCUMENTS

| | | | |
|---|---|---|---|
| 3,897,321 | 7/1975 | Blank et al. | 204/157.63 |
| 4,012,442 | 3/1977 | Blank et al. | 568/35 |
| 4,778,932 | 10/1988 | Manami et al. | 568/33 |

*Primary Examiner*—Alan L. Rotman
*Attorney, Agent, or Firm*—Richard D. Fuerle; Arthur S. Cookfair

[57] ABSTRACT

Disclosed is a method of making a chlorobenzene having the general formulas

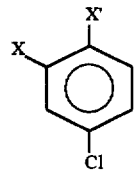

where X is Cl or F, and X' is X or CF$_3$. A compound having the formula

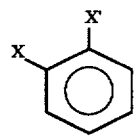

is sulfonated using at least 2 moles per mole of said compound of a sulfonating agent selected from the group consisting of sulfuric acid, chlorosulfonic acid, and mixtures thereof, to produce a sulfonated compound. The sulfonated compound is chlorodesulfonated to produce a chlorobenzene, such as 1,2,4-trichlorobenzene. Preferably, the starting material is ortho-dichlorobenzene.

20 Claims, No Drawings

METHOD OF MAKING CHLOROBENZENES

CROSS-REFERENCE TO RELATED APPLICATION

This application is related to application Ser. No. 08/654,434 filed May 28,1996, by R. Krishnamurti, titled "Method of Preparing 1,2,4-Trichlorobenzene."

BACKGROUND OF THE INVENTION

This invention relates to a method of making chlorobenzenes. In particular, it relates to a method of making 1,2,4-trichlorobenzene by sulfonating orthodichlorobenzene to produce a sulfonated compound which is then chlorodesulfonated.

The compound 1,2,4-trichlorobenzene (1,2,4-TCB) is a commercially important raw material used for producing herbicides and fungicides. It is typically obtained as a by-product during the chlorination of benzene. However, it is very difficult to obtain 1,2,4-TCB in high yield and purity because large amounts of the dichlorobenzenes must be recycled in order to minimize the formation of undesirable tetra and higher chlorinated products, and this recycling requires a large and expensive reactor. A substantial amount of 1,2,3-trichlorobenzene (1,2,3-TCB) is also produced, which must be separated from the 1,2,4-TCB.

SUMMARY OF THE INVENTION

I have discovered a method of making 1,2,4-TCB and related compounds from ortho-dichlorobenzene or related compounds. The method of this invention is a two step process involving the formation of a sulfonated compound followed by chlorodesulfonation to produce the 1,2,4-TCB or a related product. The process of this invention is isomer-selective and therefore more efficient at making 1,2,4-TCB than is the prior process of chlorinating benzene.

DESCRIPTION OF THE PREFERRED EMBODIMENTS

The starting material for the process of this invention is a compound having the general formula

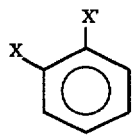

where X is Cl or F, and X' is X or $CF_3$. Preferably, X and X' are both chlorine as ortho-diclorobenzene is the more inexpensive starting material and it produces the more valuable product, 1,2,4-TCB. Ortho-dichlorobenzene is obtained commercially by chlorinating benzene in the presence of a Lewis acid catalyst such as ferric chloride.

In the first step of the process of this invention, the starting material is sulfonated using a sulfonating agent that can be either sulfuric acid, chlorosulfonic acid, or a mixture thereof. The electrophilic reaction occurs predominantly at the carbon para- to the X' group. Preferably, the sulfonating agent is sulfuric acid because it is less expensive. The sulfonation of ortho-dichlorobenzene is a known reaction. See, for example U.S. Pat. No. 4,778,932, herein incorporated by reference. Briefly, the starting compound is reacted with the sulfonating agent at a minimum molar ratio of 2 and preferably at a molar ratio of about 2.5 to about 3, as if less sulfonating agent is used sulfonic acid may be produced and more sulfonating agent is usually unnecessary. A catalyst such as phosphomolybdic acid and phosphotungstic acid is needed for this reaction. About 5 to about 15 wt % of the catalyst should be used as the reaction proceeds too slowly if less catalyst is used and more catalyst is usually unnecessary. Sulfonation will occur readily at a temperature of about 180° to about 205° C. The water produced in the reaction distills into a moisture trap as an azeotrope with o-dichlorobenzene. The heavier o-dichlorobenzene in the trap is then recycled back to the sulfonation reactor.

If the sulfonating agent is sulfuric acid and the starting compound is ortho-dichlorobenzene, the product is 3,4-dichlorophenylsulfone (3,4-DCPS), a solid which melts at about 173° to about 175° C. If the sulfonating agent is chlorosulfonic acid, the product is a mixture of about 65 mole % 3,4-dichlorobenzenesulfonyl chloride (3,4-DCBSC) and 35 mole % 3,4-DCPS; pure 3,4-DCBSC is an oil.

In the next step, the sulfonated compound (or compounds) made in the first step is chlorodesulfonated either thermally or photochemically using gaseous chlorine. Since the products of the first step are solids, they are melted or are mixed with a solvent to form a solution or a slurry. Solvents such as 1,2,4-TCB, chlorobenzene, ortho-dichlorobenzene, or 1,2,3-TCB can be used to form a solution or slurry. If the final product is 1,2,4-TCB, the preferred solvent is 1,2,4-TCB because then no subsequent separation of the solvent is required. The melt, solution, or slurry can be heated to about 50° to about 250° C.; the reaction is too slow at lower temperatures and at higher temperatures polychlorinated biphenyls may form; the preferred temperature range is about 100° to about 180° C. At least 1.1 moles of chlorine gas is pumped into the liquid per mole of the sulfonated intermediate. The process of converting 3,4-DCPS into 1,2,4-TCB occurs in two steps. In the first step, chlorine reacts stoichiometically with 3,4-DCPS to generate 1,2,4-TCB and 3,4-DCBSC. In the second step, chlorine converts 3,4-DCBSC into 1,2,4-TCB catalytically. The progress of the chlorodesulfonation reaction can be followed by gas chromatography (GC). If the product is 1,2,4-TCB (a liquid at room temperature), it can be purified by distillation (bp=215° C.). Other final products can also be purified by distillation.

The following examples further illustrate this invention.

EXAMPLE 1

Preparation of 3,4-DCBSC and 3,4-DCPS

These compounds were prepared by published procedures. Thus, 3,4-DCBSC was obtained by chlorosulfonation of 1,2-dichlorobenzene with chlorosulfonic acid as described in the literature (R. J. W. Cremlyn, T. Cronje, *Phosphorus and Sulfur,* 1979,. Vol. 6, pp. 495–504), and 3,4-DCPS was obtained by sulfonation of 1,2-dichlorobenzene with sulfuric acid using phosphomolybdic acid as catalyst as described in U.S. Pat. No. 4,778,932.

EXAMPLES 2 to 5

General Procedure for Chlorodesulfonation of 3,4-DCBSC and 3,4-DCPS

The apparatus consisted of a 3-necked flask containing a magnetic stir bar and fitted with a Friedrich condenser, a twin adapter for a thermometer and a polytetrafluoroethylene (Teflon) tube for chlorine delivery, and an adapter containing a Teflon-backed septum for sample withdrawal. The top of the condenser was connected in series with an ice-cooled empty trap (to condense any vapors that may not condense), a stirred water trap, and a stirred 10% aqueous KOH trap. Chlorine flow was regulated to the desired level using a needle valve and the flow rate was measured using a transducer.

The apparatus was purged with nitrogen for 15 minutes and the calculated quantity of the appropriate starting material was introduced into the reactor under a gentle nitrogen sweep. When no solvent was used, the starting material was melted by heating and maintained above the melting point. Cold water to the condenser was turned on, and nitrogen gas was bubbled through the material for 10 minutes. After the desired reaction temperature had been attained, nitrogen flow was stopped and chlorine was bubbled through the solution at an appropriate rate. Generally, chlorine flow was conducted intermittently at a low rate since chlorine breakthrough was observed at higher passage rates. Reaction progress was followed by withdrawing an aliquot by a syringe and quickly diluting it with dichloromethane. This solution was analyzed by gas chromatography. The following examples illustrate the chlorodesulfonation process.

EXAMPLE 2

The starting material was a 65/35 wt % mixture of 3,4-DCBSC/3,4-DCPS. A 17.1 g sample of this mixture was pre-heated to 200° C. and chlorine gas was passed at the rate of 0.02 mole/min. After 3 hours, the reaction temperature was raised to 215° C. and chlorine was passed at the same rate for another hour. GC analysis at this point indicated that the reaction mixture was 84 wt % 1,2,4-TCB, 11.8 wt % 3,4-DCBSC, and 0.4 wt % 3,4-DCPS. This mixture was then cooled to 150° C. and irradiated with an externally placed medium pressure mercury lamp while chlorine was passed at the same rate for another hour. GC analysis of the reaction mixture indicated a 94 wt % yield of 1,2,4-TCB.

EXAMPLE 3

The starting material was the same 65/35 wt % mixture of 3,4-DCBSC/3,4-DCPS used in Example 2. A 19.9 g sample of this mixture was heated to 100° C. to melt all of the solids. Chlorine gas was passed intermittently through the reactants over 3.5 hours at the rate of 0.026 mole/min. After 5 hours, GC analysis indicated that the reaction mixture contained 91 wt % 1,2,4-TCB and 8.6 wt % 3,4-DCBSC. After passing chlorine intermittently for another 2 hours, the reaction was terminated and a final aliquot was taken for GC analysis. A 97 wt % yield of 1,2,4-TCB was obtained. Significantly, no polychlorinated biphenyls were formed under these conditions.

EXAMPLE 4

The starting material was 3,4-DCPS and the reaction was conducted in 1,2,4-TCB as a solvent. A 10 g sample was suspended in 10 mL of 1,2,4-TCB and heated to 125° C. Most of the 3,4-DCPS dissolved at this point. Chlorine gas was passed intermittently through the solution over 2.5 hours at the rate of 0.025 mole/min. Then the reaction temperature was raised to 140° C. and chlorine was passed intermittently over the next 2.5 hours. GC analysis of an aliquot indicated that the yield of 1,2,4-TCB was 82 wt %. Significantly, no polychlorinated biphenyls were formed under these conditions.

EXAMPLE 5

The starting material was 3,4-DCPS and the reaction was conducted without a solvent. A 10 g sample was melted by heating it to 185° C. (bath temperature) and chlorine gas was passed intermittently through the sample over about 9.5 hours at the rate of from 0.016 to 0.026 mole/min while the heating bath was maintained at 175° to 180° C. GC analysis of an aliquot indicated that the yield of 1,2,4-TCB was 85 wt %. Significantly, no polychlorinated biphenyls were formed under these conditions. The results of Examples 2 to 5 are given in the following table.

| Example Number | Starting Material | Reaction Temp (°C.) | 1,2,4-TCB | 3,4-DCPS | 3,4-DCBSC | PCB's |
|---|---|---|---|---|---|---|
| 2 | 3,4-DCBSC/3,4-DCPS (65/35) | 200–215 | 94 | ND | <0.1 | 4.0 |
| 3 | 3,4-DCBSC/3,4-DCPS (65/35) | 100 | 97 | <0.1 | 1.8 | ND |
| 4 | 3,4-DCPS | 140 | 82 | 5.7 | 11.2 | ND |
| 5 | 3,4-DCPS | 175–180[1] | 85 | 1.7 | 12.9 | 0.15 |

[1]Indicates temperature of the oil bath;
N.D. = Not Detected.
The above experiments show that very high yields of 1,2,4-TCB are obtained with very low productions of PCB's using the process of this invention.

We claim:

1. A method of making a chlorobenzene having the general formula

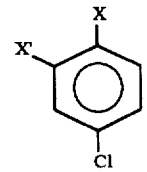

where X is C or F, and X' is X or CF$_3$ comprising (A) heating a compound having the formula

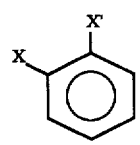

with at least 2 moles per mole of said compound of a sulfonating agent selected from the group consisting of sulfuric acid, chlorosulfonic acid, and mixtures thereof to produce a sulfonated compound; and (B) heating said sulfonated compound at about 50° to about 250° C. in the presence of at least a catalytic amount of gaseous chlorine to produce said chlorobenzene.

2. A method according to claim 1 wherein said sulfonating agent is sulfuric acid.

3. A method according to claim 1 wherein said sulfonating agent is chlorosulfonic acid.

4. A method according to claim 1 wherein X and X' are Cl.

5. A method according to claim 1 wherein the amount of said compound is about 2.5 to about 3 moles per mole of said sulfonating agent.

6. A method according to claim 1 wherein said sulfonating is at a temperature of about 180° to about 205° C.

7. A method according to claim 2 wherein phosphomolybdic acid, phosphotungstic acid, or a mixture thereof is used as a catalyst during said sulfonating.

8. A method according to claim 1 wherein said chlorodesulfonating is at a temperature of about 50° to about 250° C.

9. A method according to claim 8 wherein said chlorodesulfonating is at a temperature of about 100° to about 180° C.

10. A method according to claim 1 wherein the molar ratio of said compound to said sulfonating agent is at least 2.

11. A method according to claim 1 wherein said sulfonated compound is liquefied by melting in step (B).

12. A method according to claim 1 wherein said sulfonated compound is in a solvent in step (B).

13. A method of making 1,2,4-trichlorobenzene comprising (A) reacting 1,2-dichlorobenzene with sulfuric acid at a molar ratio of about 2.5 to about 3 in the presence of a catalyst selected from the group consisting of phosphomolybic acid, phosphotunqstic acid, and mixtures thereof at about 180° to about 205° C. to produce 3,4-dichlorophenylsulfone; and (B) reacting said 3,4-dichlorophenylsulfone with at least 1.1 moles of chlorine gas per mole of said 3,4-dichlorophenylsulfone at about 50° to about 250° C.

14. A method according to claim 13 wherein step (B) is at a temperature of about 100° to about 180° C.

15. A method according to claim 13 wherein said 3,4-dichlorphenylsulfone is mixed with a solvent in step (B).

16. A method according to claim 13 wherein said 3,4-dichlorophenylsulfone is melted in step (B).

17. A method of making 1,2,4-trichlorobenzene comprising (A) reacting 1,2-dichlorobenzene with chlorosulfonic acid at a molar ratio of about 2.5 to about 3 at about 180° to about 205° C. to produce a mixture of 3,4-dichlorobenzenesulfonyl chloride and 3,4-dichlorophenylsulfone; and (B) reacting said mixture with at least a catalytic amount of chlorine gas at about 50° to about 250° C.

18. A method according to claim 17 wherein step (B) is at a temperature of about 100° to about 180° C.

19. A method according to claim 17 wherein said mixture is mixed with a solvent in step (B).

20. A method according to claim 17 wherein said mixture is melted in step (B).

* * * * *